United States Patent [19]
Weiler

[11] Patent Number: 5,176,293
[45] Date of Patent: Jan. 5, 1993

[54] DISPENSER WITH REMOVABLE UNITARY CAP AND THREADABLE OVERCAP

[75] Inventor: Gerhard H. Weiler, South Barrington, Ill.

[73] Assignee: Automatic Liquid Packaging, Inc., Woodstock, Ill.

[21] Appl. No.: 491,214

[22] Filed: Mar. 9, 1990

[51] Int. Cl.⁵ .............................................. B67D 5/00
[52] U.S. Cl. ...................................... 222/83; 222/91; 222/541
[58] Field of Search .................. 222/541, 562, 568, 83, 222/91; 206/364, 497; 604/244, 263, 266, 212, 241, 283; 215/250, 253

[56] References Cited

U.S. PATENT DOCUMENTS

| | | | |
|---|---|---|---|
| 3,369,707 | 2/1968 | Porter et al. | 222/83 |
| 3,454,196 | 7/1969 | Hazard | 222/541 |
| 3,486,503 | 12/1969 | Porter et al. | 222/568 |
| 4,258,867 | 3/1981 | Weiler et al. | 222/541 |
| 4,723,687 | 2/1988 | Kutterer | 222/91 |

Primary Examiner—Andres Kashnikow
Assistant Examiner—Philippe Derakshani
Attorney, Agent, or Firm—Dressler, Goldsmith, Shore, Sutker & Milnamow, Ltd.

[57] ABSTRACT

A douche or enema dispenser is provided as a unitary hermetically sealed container and a cooperating overcap. The container has a cap structure which is removable by torsion applied through the overcap positioned over the cap structure, engageable with the adjacent container neck portion, and simultaneously rotatable as well as axially movable relative thereto. As the overcap is rotated relative to the neck portion, ribs in the overcap engage tip portions of a wing member associated with the cap structure. Since the cap structure is mounted over and sealed about a frangible web located around the container mouth that is located at the distal end of the neck portion, when sufficient torsion develops, the web is fractured, the cap is removed, and the container is opened. In opening the container, force upon walls of the liquid-filled body portion of the container is minimized.

11 Claims, 6 Drawing Sheets

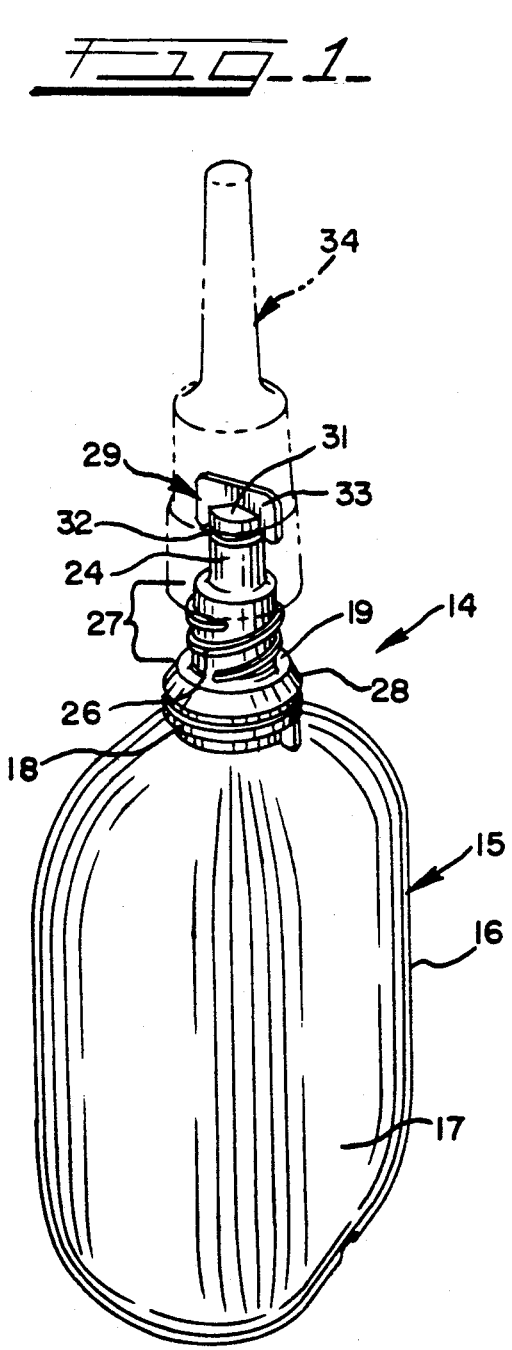
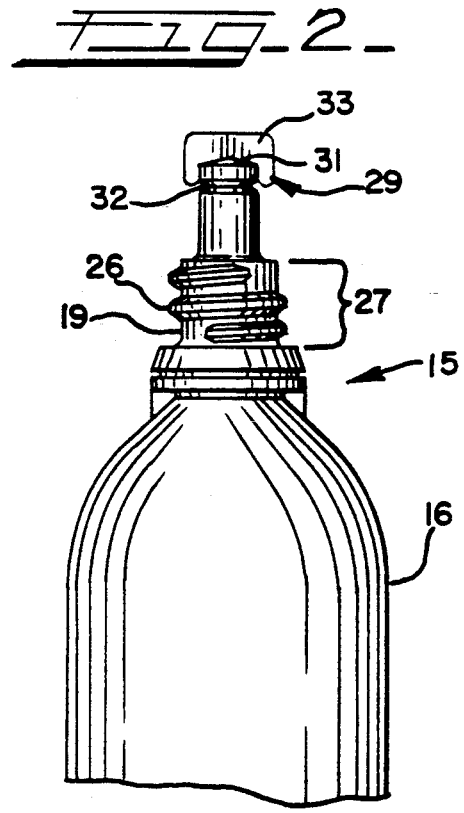
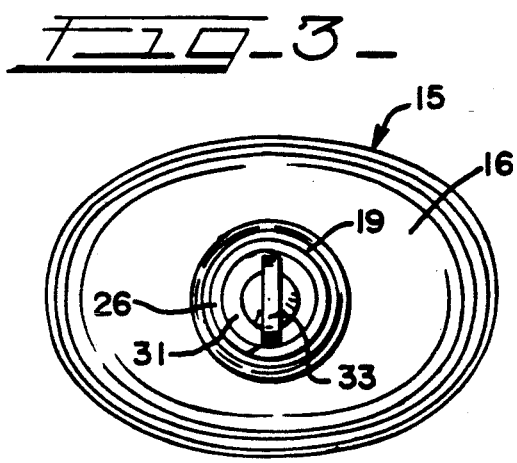

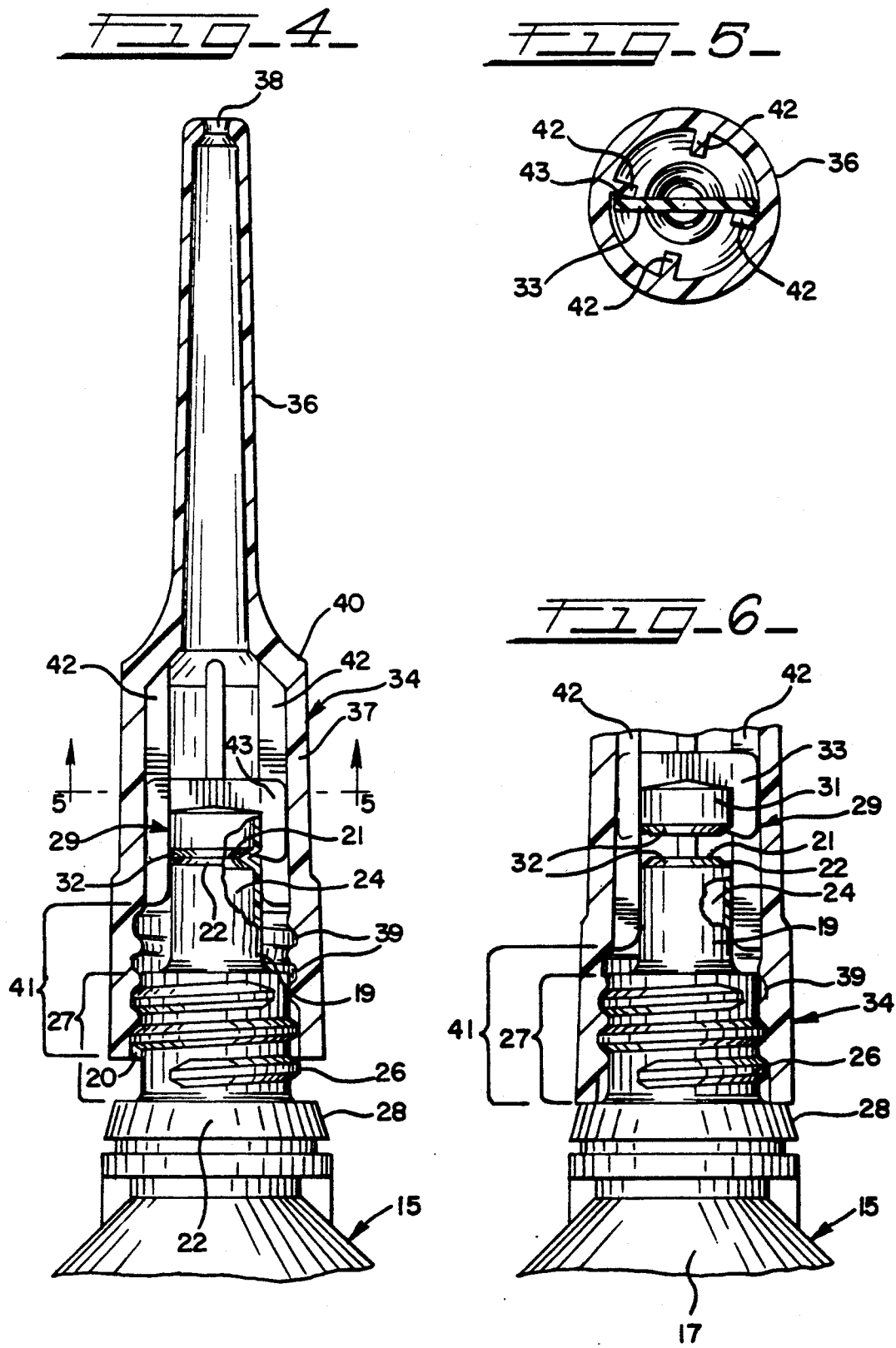

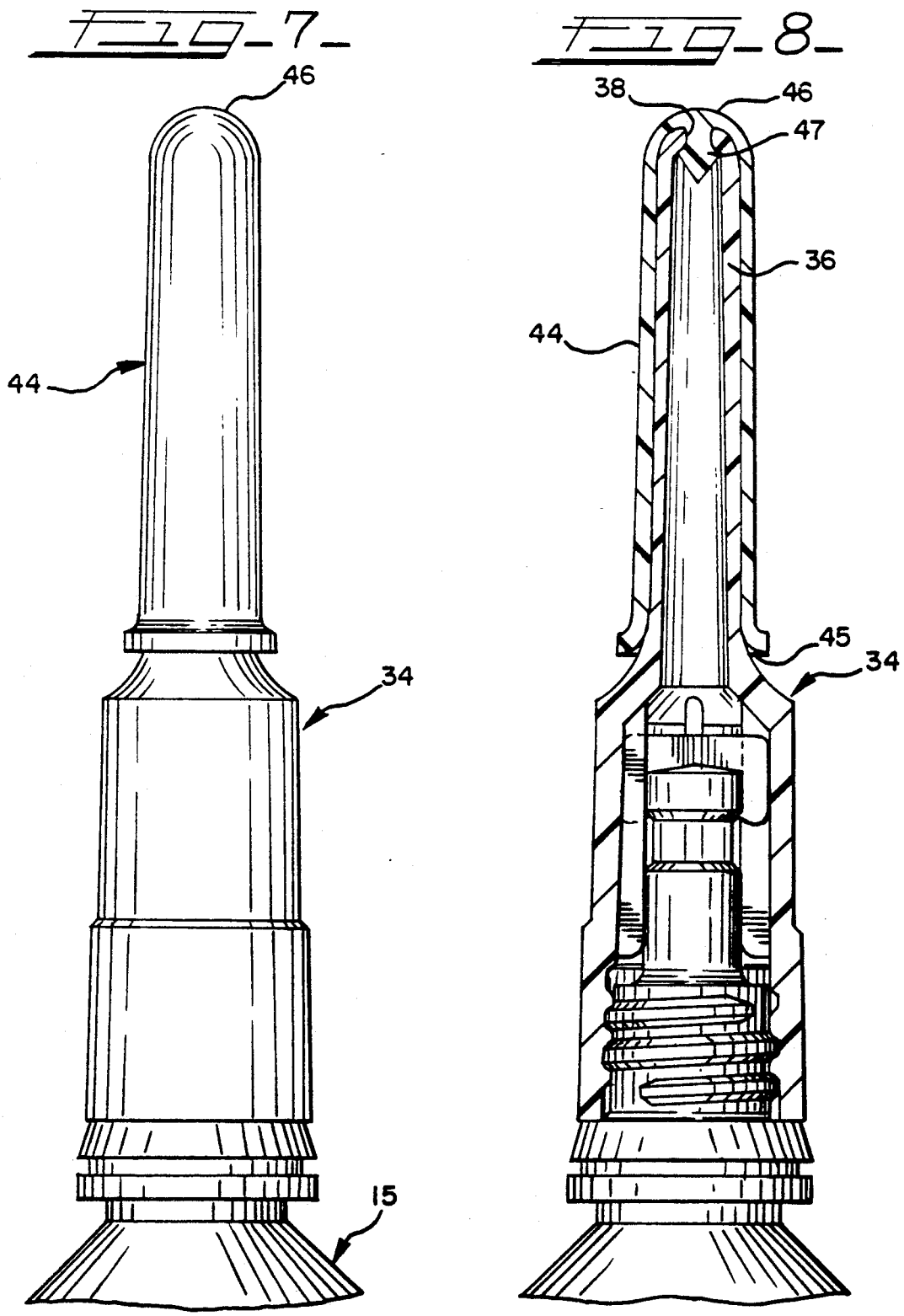

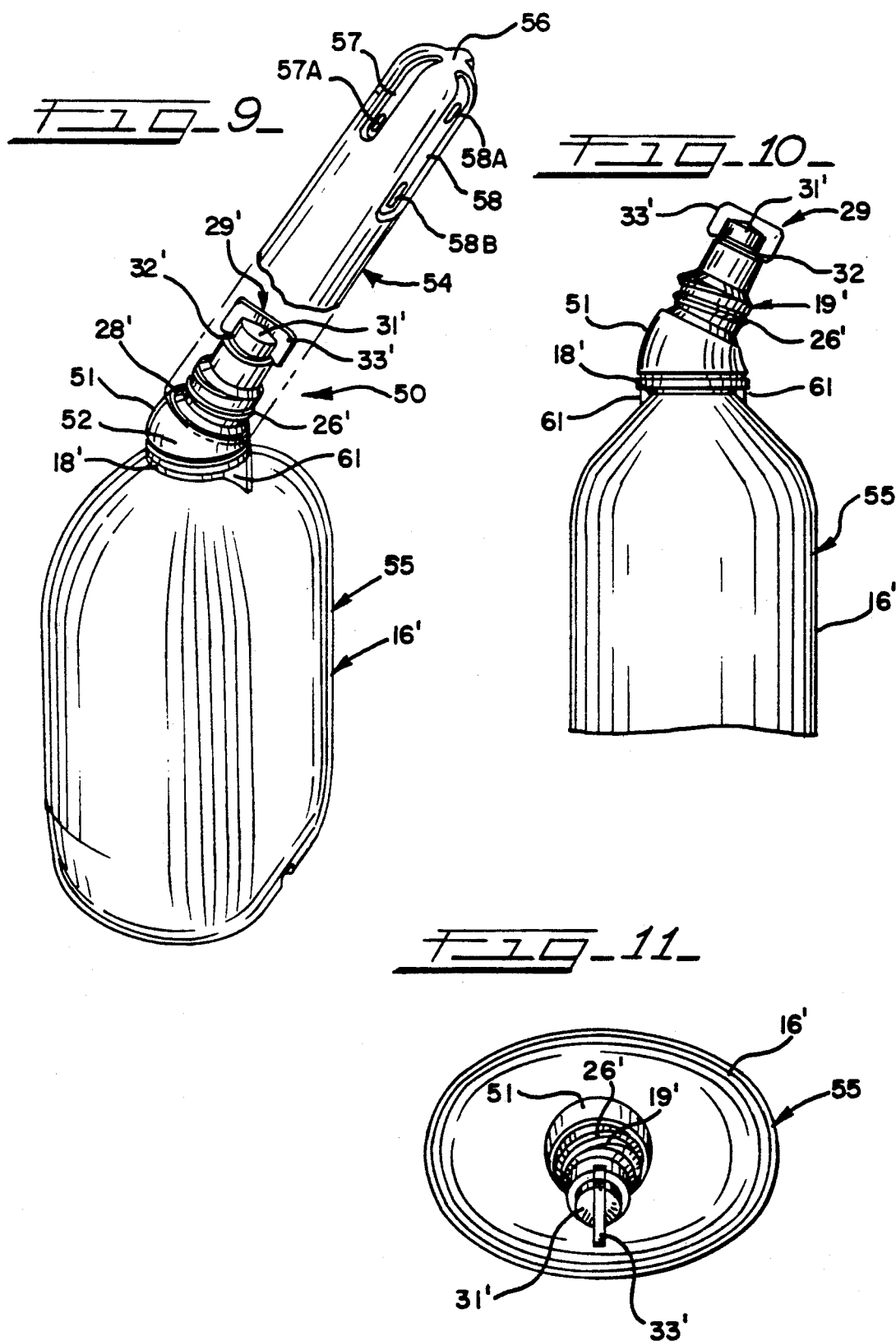

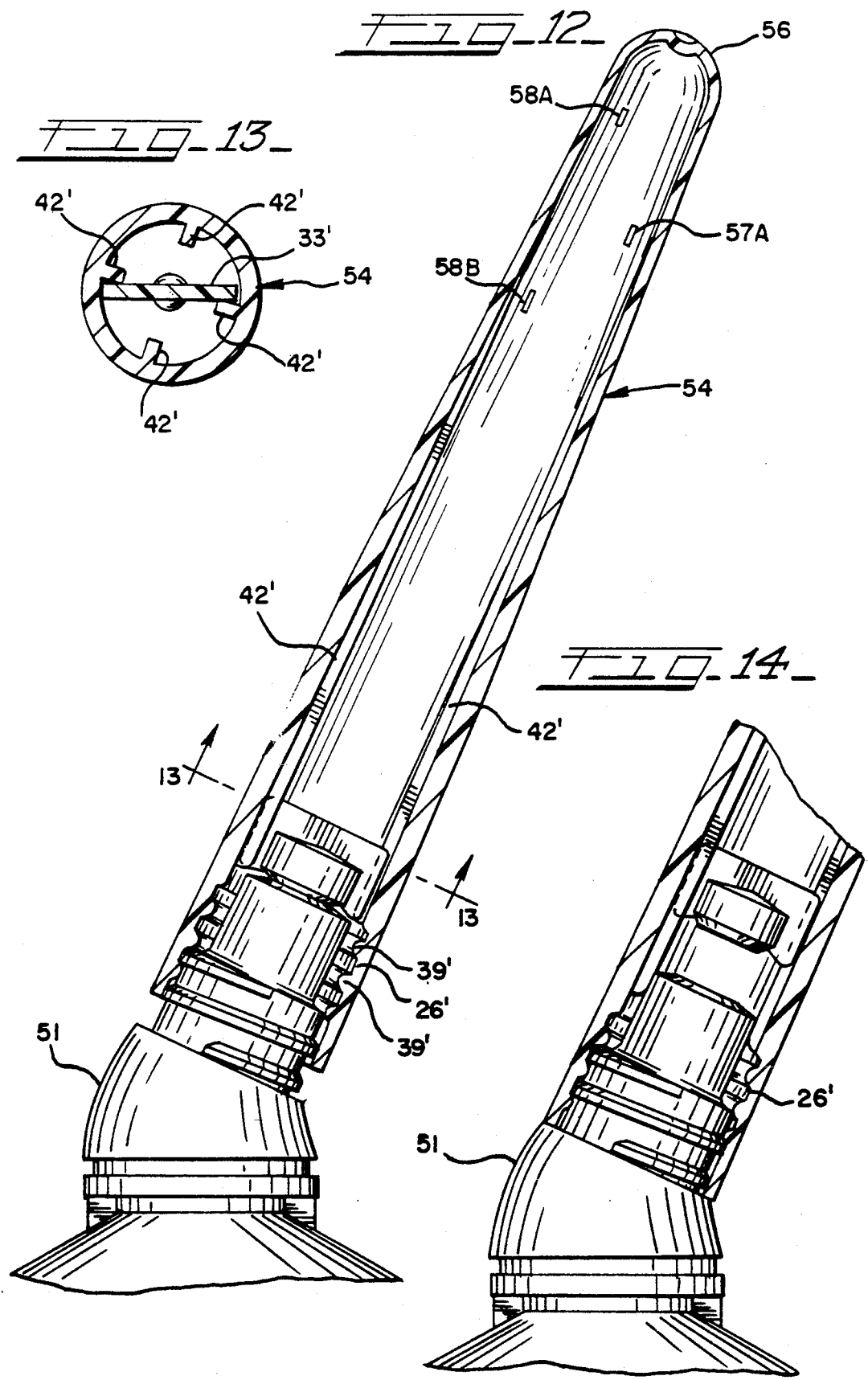

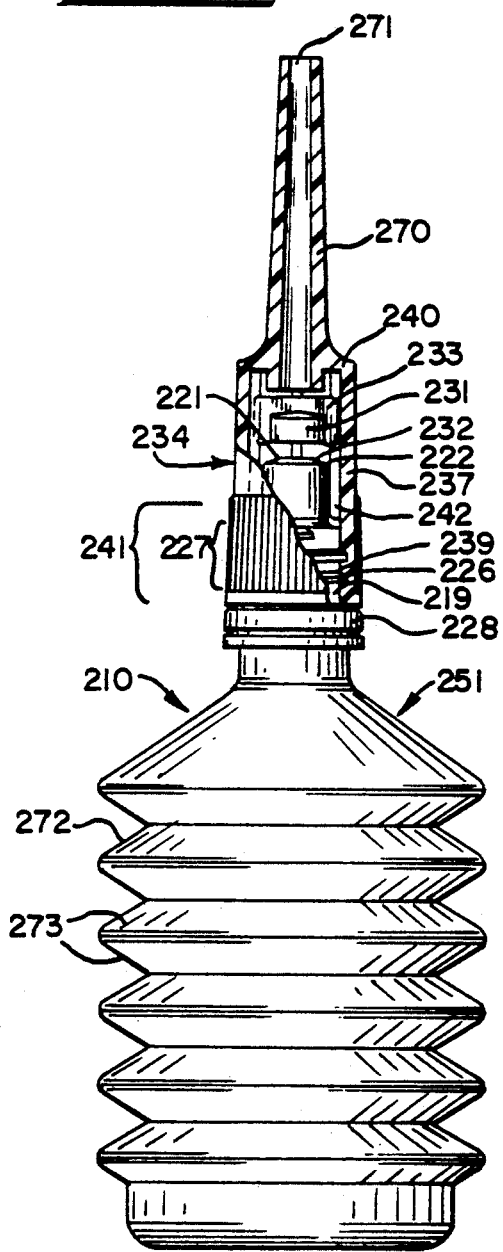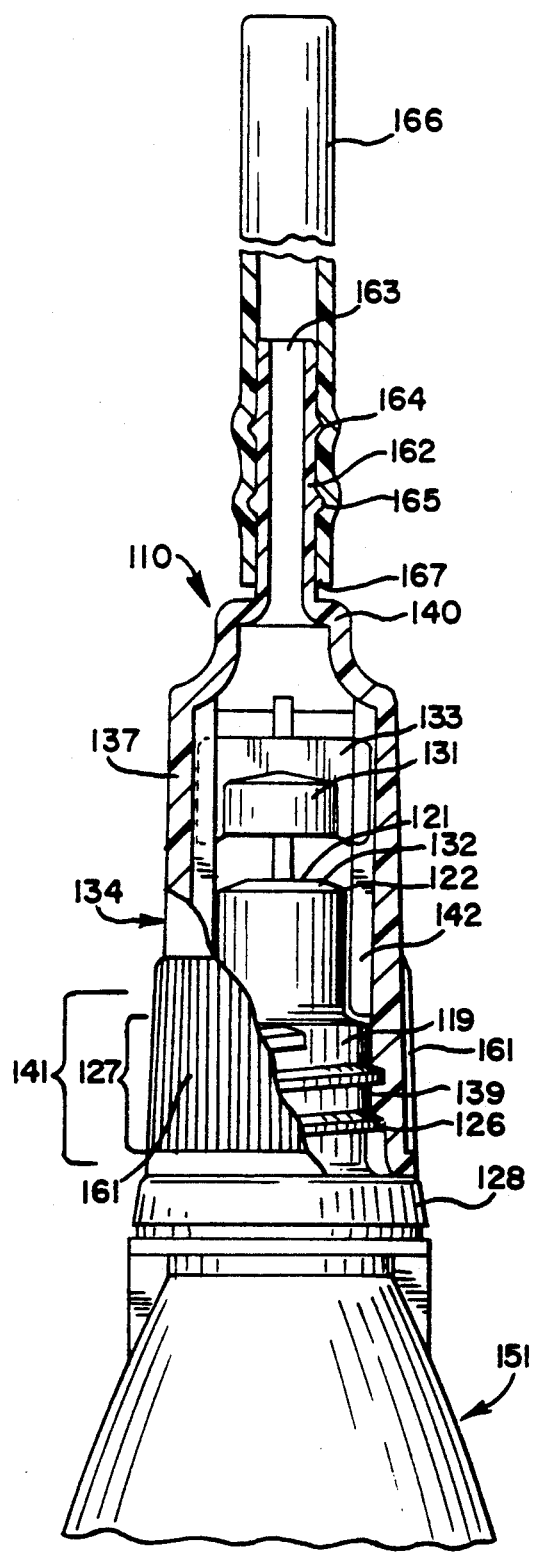

DISPENSER WITH REMOVABLE UNITARY CAP AND THREADABLE OVERCAP

FIELD OF THE INVENTION

This invention relates to a hermetically sealed container having a unitary closure cap and provided with a threadably engaged overcap for torsional removal of the cap without squeezing the container itself.

BACKGROUND OF THE INVENTION

Hermetically sealed containers made by a form-fill-and-seal process are known. The closure portion for such containers incorporates a unitary but removable cap situated over a container mouth at the neck portion distal end. The cap is removable by fracturing, with manually applied force, a frangible unitary web located between the cap and the container neck portion. The container manufacturing technique is well known, and is described in U.S. Pat. No. 4,176,153 to Weiler et al.

Commonly assigned U.S. Pat. No. 4,258,867 to Weiler et al. describes one such container which can be formed, filled with a liquid, and then sealed, all under continuous, commercial scale, high speed, sterile, manufacturing conditions.

For reasons associated with a desire to provide a container the contents of which can be manually compressed and distorted as an aid for dispensing a liquid fill, the walls of such a container are typically made as thin as practical. However, a problem arises when one follows the normal or intended procedure for opening such a container with manually applied force. The applied force inherently involves gripping while compressing, at least in part, the container itself. Consequently, when frangible web fracture occurs loosening the container cap, liquid contents of the container surge out through the opened container mouth before the user can relinquish the applied force. This surge usually results in an undesirable spillage and wastage of some of the liquid contents.

It would be desirable to have a hermetically sealed container that can be opened by fracturing the frangible web without using an applied force which results in such a wasteful liquid contents surge. The present invention fulfills such need.

SUMMARY OF THE INVENTION

The present invention provides a new and useful dispenser comprising, in combination, a hermetically sealed container and a cooperative hollow overcap rotatably and threadably engaged with the container closure. Rotation of the overcap relative to the container produces relative axial movement and torsion which removes the container cap without compressive forces being applied to the container body. Thereafter, the overcap directs fill liquid discharge by means of a built-in nozzle. Such dispensers are useful, inter alia, for single use douche and enema compositions. Configuration of the built-in nozzle is determined by the contemplated end use.

The sealed container includes a body portion, a unitary neck portion extending outwardly from the body portion and terminating distally in a container mouth, and a closure portion about the mouth and unitary therewith. The closure portion includes a unitary cap positioned over the mouth and a frangible web that joins the cap to the neck portion about the mouth.

The container neck portion adjacent to container body portion additionally has external screw threads formed therein. These threads can be left-handed or right-handed, and extend circumferentially about an outside wall portion thereof. The threads are longitudinally spaced from the container mouth for a predetermined distance.

The overcap is elongated, hollow, and in the assembled dispenser covers both the closure portion and also adjacent regions of the neck portion. The overcap is rotatable about the neck portion by virtue of internal screw threads which are threadably engageable with the neck portion screw threads. The overcap also has longitudinally extending, peripherally spaced internal rib means adjacent to but inwardly from the internal threads.

The unitary container closure cap has radially outwardly extending wing means that are engageable by the longitudinally extending unitary rib means on an inside surface of the overcap. The overcap is first threadably received on the neck portion before the wing means or members come to rest against and engage such rib means. Further advancement of the overcap onto the neck portion by threading twists the wing means and severs the unitary closure cap from the container.

Thus, threading of the overcap onto the neck portion applies torsion upon the cap by coaction of closure wing means with the overcap rib means. This torsion fractures the frangible web, thereby separating the closure cap from the container mouth, and thus opening the container without a distorting force being exerted upon the body portion of the container.

Once the container has been so opened, the hollow overcap, if provided with a through passageway, can perform yet another function. While a sealing engagement is provided between the overcap and the neck portion in the region of the engaged threads, the overcap itself then provides a fill liquid distribution and dispensing nozzle. In this manner, delivery and discharge of fill liquid from the container can be localized and directed to a desired delivery site or location, such as in a body cavity, or the like.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

BRIEF DESCRIPTION OF THE DRAWINGS

In the drawings:

FIG. 1 is a perspective view of an enema dispenser embodying this invention and showing a hermetically sealed container in association with a hollow, cooperative overcap, the overcap being shown in phantom for illustration purposes;

FIG. 2 is an end elevational view of the container of FIG. 1 wherein lower portions of the liquid holding vessel portion of such container are broken away, and wherein the overcap is removed;

FIG. 3 is a top plan view of the container of FIG. 1 with the overcap removed;

FIG. 4 is a view similar to FIG. 2, but showing the overcap in cooperative association with the container neck portion and closure portion and with the overcap rotated to the position where overcap ribs first engage cap wings, some parts thereof being broken away, and the overcap being shown in longitudinal section; and FIG. 5 is a transverse sectional view taken along the plane 5—5 of FIG. 4;

FIG. 6 is a fragmentary view similar to FIG. 4, but showing the relative position of the overcap in relation to the assembled container neck portion and closure portion after the frangible web has been fractured and the cap separated from the mouth of the neck portion by rotation of the overcap relative to the neck portion, some parts thereof being broken away;

FIG. 7 is a fragmentary side elevational view of the dispenser wherein the overcap is in functional association with a cooperative cover;

FIG. 8 is a sectional elevation of the dispenser portion shown in FIG. 7;

FIG. 9 is a perspective view of a douche dispenser embodying this invention showing a hermetically sealed container in association with a cooperating overcap, the overcap being shown partially in phantom for illustration purposes;

FIG. 10 is a fragmentary elevational view of the container of FIG. 9 wherein the overcap is removed;

FIG. 11 is a top plan view of the container of FIG. 10;

FIG. 12 is an view, enlarged fragmentary that of partly in section, showing the overcap of FIG. 10 in cooperative association with the container neck portion and closure portion, and with the overcap rotated to the position wherein overcap ribs first engage cap wings;

FIG. 13 is a transverse sectional view taken along the plane 13—13 of FIG. 12;

FIG. 14 is a fragmentary view similar to FIG. 12 showing the relative position of the overcap in relation to the assembled container neck portion and closure portion after the frangible web has been fractured and the unitary cap separated from the container neck portion by rotation of the overcap relative to the neck portion;

FIG. 15 is a view similar to FIG. 4, but showing an alternative embodiment of the overcap; and FIG. 16 is a side elevational view showing an alternative embodiment of the overcap in association with an alternative embodiment of a hermetically sealed container, portions of the overcap being broken away to show interior detail.

DESCRIPTION OF THE PREFERRED EMBODIMENTS

Referring to FIGS. 1 through 7, enema dispenser 14 embodying this invention comprises a hermetically sealed container 15 and an overcap 34 associated therewith. Container 15 is of unitary construction and includes a body portion 16 whose walls are relatively thin and which define a liquid-holding cavity 17. Body portion 16 and cavity 17 can have any convenient or desired configuration. The container configuration shown, however, is presently preferred, particularly with the body portion 16 sized to fit into the palm of an average or typical adult human hand. The walls of body portion 16 are relatively thin so that body portion 16 can be manually squeezed, i.e., compressed and distorted to dispense a liquid fill therefrom.

Container 15 can be molded using a thermoplastic polymer. Presently preferred such polymers are low density polyethylene (LDPE), very low density polyethylene (VLDPE), polypropylene (PP), and the like. The thickness of the walls of vessel portion 16 can vary from one location to another, but are preferably formed as thin as practical, consistent with structural strength requirements.

Container 15 can be made by a parison molding procedure wherein body portion 16 is formed first, then charged with a desired liquid fill, and thereafter immediately sealed by formation of the neck and closure portions of the container 15. The forming, filling, and sealing operations are carried out automatically under sterile conditions using the procedures known to the art.

One end 18 of body portion 16 terminates in a tapered neck portion 19 which is unitary with body portion 16. Neck portion 19 defines therein a mouth 21 (see FIG. 6) at the distal end 22 thereof. A channel 24 extends between such mouth 21 and cavity 17 in neck portion 19 to provide communication with body portion 16. The neck portion 19 and the body portion 16 usually are positioned substantially symmetrically about a common longitudinal axis, as shown.

External screw threads 26 are formed about the periphery of neck portion 19. The threads 26 extend circumferentially outwardly about an outside wall region 27 of neck portion 19. As shown in FIGS. 4 and 5, the region 27 is adjacent the proximal end or base 28 of neck portion 19. The threaded region 27 has a relatively larger diameter than the unthreaded distal part of neck portion 19. External screw threads 26 begin on the neck portion at a location that is in longitudinally spaced relationship to mouth 21 toward container body portion 16. Screw threads 26 can be left-handed or right-handed, as desired.

A unitary closure portion 29 for container 15 is located at distal end 22 of neck portion 19. Closure portion 29 includes a removable, but initially unitary closure cap 31 which overlies and seals the mouth 21. The cap 31 can have various configurations, but the cylindrical form shown is presently preferred. Frangible web 32 that is unitary with cap 31 and distal end 22 is located about the mouth 21. Closure portion 29 also includes an upstanding wing member 33 unitary therewith that extends radially outwardly from the longitudinal axis of neck portion 19. The wing member 33 can have various configurations, but the longitudinally flattened form shown is presently preferred.

A separately formed, elongated and hollow overcap 34 (see FIG. 4) defines a central passage having an entry orifice 20 and a dispensing orifice 38 and is positioned in the assembled container 15 over the closure portion 29 and also over at least an adjacent part of neck portion 19. Preferably, and as shown, overcap 34 extends from the distal end 22 of neck portion 19 to the proximal end 28 thereof. Overcap 34 can be made of a relatively rigid molded thermoplastic polymer, such as ethylene vinyl acetate (EVA), or the like. Such thermoplastic polymer can be pigmented, as is presently preferred, to contrast the appearance thereof in relation to the preferred transparent or translucent appearance of container 15.

The overcap defines a nozzle means through which liquid contents from body portion 16 is dispensed after mouth 21 is opened. The nozzle means is provided by a unitary, forwardly extending tubular stem extension 36 which projects axially from the distal terminus 40 of the skirt portion 37 of overcap 34. The free or distal end of tubular stem extension 36 terminates in a dispensing orifice 38.

Overcap 34 at its skirt portion 37 is provided with internal screw threads 39 about an inside region 41 adjacent to orifice 20. The overcap screw threads 39 are threadably engageable with the neck portion screw threads 26.

Ribs 42 are peripherally spaced from one another along the inside wall of overcap 34 and extend radially inwardly to surround neck portion 19 above threaded region 27. Ribs 42 are adapted to engage wing member 33 of closure cap 31 upon threaded engagement of overcap 34 with neck portion 19. The ribs 42 preferably extend longitudinally somewhat above the mouth 21 when the overcap 34 is fully threadably engaged with the neck portion 19 as shown, for example, in FIG. 6. An opposed pair of the ribs 42 is preferably arranged so that each rib thereof is abuttable against a different radially opposed edge part of the wing member 33 when the overcap 34 is threadably engaged over the neck portion 19 and the overcap 34 is rotated relative to the neck portion 19 to achieve a position such as illustrated, for example, in FIGS. 4 and 5. At least one pair of ribs 42 is present. Preferably four ribs, evenly spaced about the inner periphery of overcap 34, are used so that not more than about one quarter of one full 360° turn or rotation of overcap 34 relative to container 15 is needed before wing member 33 comes into abutting engagement with a pair of opposed ribs 42.

For purposes of achieving symmetrical torque application against wing member 33, at least two opposed ribs 42 should be used, and such a rib pair in the embodiment shown is located with respective ribs of such pair being at diametrically opposed locations in overcap 34 so that each such rib 42 is engageable with a different opposite side extension of the wing member 33 (see, for illustration, FIG. 5). Each rib 42 preferably has generally straight, radially inwardly extending sides to provide complementary surface areas thereof which abut against, and are slidably engageable upon axial movement relative to the opposite side extensions of the wing member 33. The longitudinal distance between the beginning of overcap screw threads 39 and the inner overcap region 43 along ribs 42 where such opposite side extensions of wing member 33 initially abut when the threadable engagement between neck portion screw threads 26 and overcap screw threads 39 is achieved is at least equal to the longitudinal distance across the neck portion screw threads 26 and region 27.

Thus, when overcap 34 is positioned over closure portion 29 and neck portion 19, and such threadable engagement between respective screw threads 26 and 39 is begun, rotation of overcap 34 relative to neck portion 19 in a direction which increases the amount of such threadable engagement produces torsion upon the wing member 33 from ribs 42, thereby creating an applied torque upon wing member 33 which is transmitted through cap 31 and applied to frangible web 32. The torsion force which develops during such relative rotation is sufficient to fracture web 32 and separate closure cap 31 from mouth 21, thereby opening container 15.

The unthreaded region of neck portion 19 is generally circular in cross-section about its longitudinal axis. The overcap 34 preferably mounts about neck portion 19 for rotation about such longitudinal axis of neck portion 19. Further, the cap 31 is preferably centered on such longitudinal axis. Wing member 33 preferably extends diametrically through such longitudinal axis and is adapted to engage at its lateral opposed edge parts two of the ribs 42.

After cap 31 is separated from mouth 21 by fracture of web 32 (see FIG. 6), cap 31 can slide within overcap 34 along ribs 15 away from distal end 22 and mouth 21 so as to provide a free flow path for liquid exiting mouth 21 from container cavity 17, particularly when the mouth 21 is in an inverted configuration relative to cavity 17. When container 15 is in an upright position with mouth 21 uppermost after fracture of web 32, the cap 31 can rest over mouth 21 (rest position not shown). Cap 31 also can act as a check valve tending to limit return of dispensed liquid to mouth 21.

Container 15 is opened by grasping the base or proximal end region 28 of neck portion 19 between the fingers of one hand and turning (rotating) the overcap 34 with the fingers of the other hand. Thus, no force need be applied against vessel portion 16 during the procedure for opening mouth 21 by fracturing web 32. Alternatively, the container 5 itself can be gently grasped while the overcap 34 is turned.

After web 32 has been fractured by rotation of overcap 34 relative to neck portion 19, the overcap 34 has so advanced into threadable engagement with neck portion 19 that overcap 34 is sealingly engaged with neck portion 19 in the region of integrated screw threads 39 and 26 (see FIG. 6). The screw threads 39 and 26 are preferably beveled or angled relative to each so that such a sealing engagement therebetween is achieved at the point or location where fracture of web 32 occurs. Also, when such a sealing engagement is achieved, the proximal end 28 of overcap 34 rests against a shelf-like projection formed in the proximal end region of neck portion 16 adjacent wall section 27. Thus, when the web 32 is fractured, liquid is dispensed from cavity 17 through mouth 21 into the central channel defined in overcap 34 when container 15 is squeezed and exits from the nozzle opening 38.

In general, the overcap 34 helps adapt a dispenser of this invention for use in a given application. For example, overcap 34 with its stem extension 36 adapts the dispenser 14 as it is duly comprised of the combination of container 15 and overcap 34 for use in the administration of enemas. For such a purpose, the stem extension 36 is preferably coated with a lubricant (not shown), such as petroleum jelly, or the like.

In a preferred enema dispenser embodiment, the overcap 34 is initially provided with an overfitting protective sleeve 44, such as shown in FIGS. 7 and 8. Sleeve 44 is closed at its distal end 46, but internally, at such distal end 46 thereof, there is provided an axially inwardly projecting barbed fitting or plug 47 which is configured to snap fit into the nozzle orifice 38 in stem extension 36 of overcap 34 to keep sleeve 44 in place until its removal.

Although container 15 is shown with a neck portion 19 which is generally axially aligned with the longitudinal axis of container body portion 16, other neck arrangements can be used, if desired. For example, referring to FIGS. 9 through 14, there is shown a douche dispenser 50 which incorporates a hermetically sealed container 55 of similar design and a cooperative overcap 54 carried on a neck portion 19' at an acute angle with respect to the longitudinal axis of container body portion 16'. Such container 55 is similar to container 15. Similar components thereof are similarly numbered, but with the addition of prime marks thereto for identification purposes.

In container 55, a hollow elbow portion 51 is unitarily included, between the base 28' of neck portion 19' and the adjoining end 18' of body portion 16' so that the neck portion 19' angularly extends from elbow portion 51, as shown. The elbow portion 51 is provided with a channel 52 extending lengthwise therethrough which interconnects the cavity 17' with the channel 24'. To aid in rigidifying and strengthening neck portion 19', a pair of opposed ribs 61 is provided between neck 52 and end 18, the ribs 61 being unitarily formed with neck portion 19' and body portion 16'.

Container 55 utilizes an overcap 54 having plural dispensing apertures in its tip. Like overcap 34, overcap 54 is provided with overcap screw threads 39', and with ribs 42' that function in the same manner as heretofore described. However, overcap 54 employs a different nozzle means. Overcap 54 is tapered longitudinally in the region thereof between the overcap screw threads 39' and the distal end 56 thereof. A plurality of longitudinally extending, exterior grooves 57 are defined in exterior or outer surface portions of overcap 54 (see FIG. 9). These grooves are circumferentially spaced equidistant from one another and located adjacent distal end 56. In overcap 54, four such equally spaced grooves, such as grooves 57 and 58, are employed. One opposed pair of such grooves identified as grooves 58 in FIG. 9, is substantially longer than the other opposed pair of such grooves, identified as grooves 57 in FIG. 9. Along the longitudinal bottom portion of each groove 58 two orifices 58A and 58B (see FIGS. 9 & 12) are provided. Similarly, orifice 57A is provided at the proximal end of each groove 57. In grooves 58, orifice 58A is provided at or near the distal end of each groove, and the second orifice 58B is provided adjacent the proximal end of each such groove. The single orifice 57A in each groove 57 is located at a longitudinal position along overcap 54 which is about midway between the longitudinal position of each pair of orifices 58A and 58B in each groove 58.

The overcap 54 is adapted to be sealingly engaged with neck portion 19' between the respective overcap screw threads 39' and neck portion screw threads 26' at the position of overcap 54 relative to neck portion 19' when fracture of frangible web 32' occurs while overcap 54 is threadably engaged with neck portion 19' and rotated relative thereto. Thus, when web 32' is fractured by torsion, and liquid exits mouth 21' from cavity 17', such liquid is generally uniformly dispensable from the individual orifices 58 particularly when the neck portion 19' is inverted relative to vessel portion 17' and the body portion 16' is manually compressed.

The dispenser 50 comprised of container 55 and associated overcap 54 is well adapted for use as a female douche, as those skilled in the dispenser art will appreciate.

However, if desired, the overcap 54 can be used in place of the overcap 34 in container 15, or the overcap 34 can be used in place of the overcap 54 in container 50.

The circumstance that the free end of an overcap nozzle means can have a configuration that is determined mainly by the contemplated use of a dispenser of this invention is further illustrated by the two further dispenser embodiments shown in FIGS. 15 and 16, respectively. In these embodiments, the overcap and the container function similarly to the overcap 34 and the container 15 in dispenser 14. Parts identified by 100-series or 200-series numerals that are similar to parts described hereinabove have been assigned numerals having the same last two digits.

Thus, in FIG. 15, there is seen a dispenser 110 having an overcap 134 which is in cooperative threaded association with the neck portion 119 of a previously hermetically sealed container 151. Overcap 134 is shown after it has been rotated about neck portion 119 to the position shown in FIG. 15 where the frangible web 132 has been fractured and the cap 131 has been thereby separated from the mouth 121 at the distal end 122 of neck portion 119 of container 151.

Overcap 134 is provided with a unitary, forwardly extending tubular stem extension 162 which protects axially from the distal terminus 140 of the skirt portion 137 of overcap 134. The open distal end 163 of stem extension 162 provides a dispensing orifice. Stem extension 162 is additionally provided with unitary radially outwardly projecting, circumferentially extending, axially spaced barbs 164 and 165 for retaining thereon a flexible extension tube 166. Although two such barbs 164 and 165 are employed in stem 162 as shown, an embodiment of overcap 134 may contain more or less than two such barbs, if desired, and various barb configurations may be used. Such barbs function to seal and seat against contiguous interior surface portions of an elastomeric delivery tube 166. End portion 167 of tube 166 is slidably extended over distal end 163 down to a position where it is in an axially spaced, adjacent relationship to the distal terminus 140. The length of tube 166 can vary, depending upon the end use application intended, for example, to permit such liquid to be discharged at a desired location in an intestine relatively remotely interiorly situated. Superficial gripping ribs 161 are provided circumferentially about the exterior of skirt portion 137 adjacent the distal end of overcap 134.

FIG. 16 depicts a dispenser 210 having an overcap 234 in cooperative threaded association with hermetically sealed bellows container 251. Overcap 234 is similar to overcap 34. Overcap 234 is shown after it has been rotated about neck portion 219 to the position shown in FIG. 16 where the frangible web 232 has been fractured and the cap 231 has been thereby separated from the mouth 221 at the distal end 222 of neck portion 219 of container 251.

Overcap 234 is provided with a unitary forwardly extending tubular stem extension 270 which projects axially from the distal terminus 240 of the skirt portion 237 of overcap 234. The open, distal end 271 of stem extension 270 provides a dispensing orifice.

The container 251 has an axially collapsible bellows-type body 272 which is unitary with the generally cylindrical neck portion 219. The body 272 is formed with a series of circumferentially extending, axially adjacent, flexible pleats 273 which permit body 272 to be collapsed upon application of an axially exerted compressive force thereto once the cap 231 has been separated from the mouth 221.

Each of the dispensers 110 and 210 is provided with respective buttress threads 126, 139 and 226, 239. Thus, each such thread has a forward face which is perpendicular to the screw axis and whose back face is at an angle to such axis so that such thread is both efficient in transmitting power and strong.

Although the present invention has been described and illustrated based on the presently available information and embodiments, it is to be understood that modifications and variations are within the spirit and scope of the invention, as those skilled in the art will readily appreciate and that such are within the purview and scope of the appended claims.

I claim:

1. A dispenser comprising, in combination, a hermetically sealed unitary container having a removable but unitary cap and a cooperative elongated, rotatable and axially movable overcap means for said cap;

said container including a body portion, a neck portion with circumferentially extending external thread means, and a closure portion at the distal end of said neck portion;

said closure portion including said unitary cap, a frangible web between said cap and said neck portion, and wing means extending from said cap;

said overcap means being positioned over said closure portion and said neck portion and including internal thread means engageable with said neck portion thread means and longitudinal internal rib means engageable with said wing means;

said unitary cap being spaced from said external thread means on said neck portion along a distance at least as great as the longitudinal length dimension of the internal thread means in said overcap means;

whereby rotational threading movement of said overcap means relative to said neck portion fractures said frangible web.

2. The dispenser of claim 1 wherein said overcap means is hollow, defines a through passageway therewithin and sealingly engages said neck portion in the region of said threadable engagement when said frangible web is fractured, and wherein said overcap means terminates at the distal end thereof in a nozzle means that defines an aperture for directing the discharge of fill liquid from said body portion when said frangible web is fractured.

3. The dispenser of claim 1 wherein said internal rib means is at least one pair of opposed ribs that extend inwardly into said overcap means.

4. The dispenser of claim 1 wherein the neck portion is substantially axially aligned with the longitudinal axis of the container body portion.

5. The dispenser of claim 1 wherein the neck portion is at an acute angle relative to the longitudinal axis of the container body portion.

6. The dispenser of claim 1 wherein said overcap means is hollow, defines a through passageway therewithin and terminates at the distal end thereof in a dispensing nozzle, and wherein an overfitting protective sleeve is provided on said dispensing nozzle.

7. The dispenser of claim 6 wherein a lubricant is contained between said dispensing nozzle and said protective sleeve.

8. The dispenser of claim 6 wherein an internal plug on said protective sleeve removably engages a dispensing orifice in said nozzle.

9. The dispenser of claim 1 wherein said overcap means is hollow, defines a through passageway therewithin, and terminates at the distal end thereof in a dispensing orifice, and wherein said overcap has adjacent said distal end thereof a stem extension defined therein, and said stem extension is provided with unitary, radially outwardly extending barb means over which a tube is slidably receivable onto said stem extension.

10. The dispenser of claim 1 wherein said overcap means is hollow, defines a through passageway therewithin, and terminates at the distal end thereof in a dispensing orifice, and wherein said container has an axially collapsible body portion.

11. The dispenser of claim 10 wherein said collapsible body portion has a side wall that is comprised of a series of circumferentially extending, axially adjacent, flexible pleats.

* * * * *